United States Patent [19]

Haag et al.

[11] Patent Number: 4,906,671
[45] Date of Patent: Mar. 6, 1990

[54] FISCHER-TROPSCH PROCESS

[75] Inventors: Werner O. Haag, Lawrenceville; James C. Kuo, Cherry Hill, both of N.J.; Paul B. Weisz, Yardley, Pa.

[73] Assignee: Mobil Oil Corporation, New York, N.Y.

[21] Appl. No.: 18,657

[22] Filed: Feb. 25, 1987

Related U.S. Application Data

[63] Continuation-in-part of Ser. No. 770,544, Aug. 29, 1985, abandoned.

[51] Int. Cl.$^4$ .............................................. C07C 1/04
[52] U.S. Cl. ..................... 518/713; 518/714; 518/715; 518/717; 518/721; 518/728
[58] Field of Search ............... 518/713, 714, 715, 716, 518/717, 728, 721

[56] References Cited

U.S. PATENT DOCUMENTS

| | | | |
|---|---|---|---|
| 4,086,262 | 4/1978 | Chang et al. | 518/719 |
| 4,159,945 | 7/1979 | Haag et al. | 518/716 |
| 4,207,250 | 6/1980 | Butler et al. | 518/719 |
| 4,255,349 | 3/1981 | Butler et al. | 518/719 |
| 4,338,089 | 7/1982 | Schaper et al. | 518/714 |
| 4,595,702 | 6/1986 | Chu et al. | 518/713 |

Primary Examiner—Howard T. Mars
Attorney, Agent, or Firm—Alexander J. McKillop; Charles J. Speciale; Howard M. Flournoy

[57] ABSTRACT

An improved Fischer-Tropsch process for hydrocarbon synthesis operated in the fluid mode of the Sasol's Synthol Process provides increased diesel and heavier hydrocarbon yield wherein a Fischer-Tropsch synthesis catalyst modified by a minor amount of a zeolite catalyst selectively converts enough waxy product to prevent adhesion between catalyst particles which might interfere with catalyst flow thereby permitting maximization of diesel oil and heavy hydrocarbon yield.

34 Claims, No Drawings

FISCHER-TROPSCH PROCESS

CROSS REFERENCE OF THE RELATED APPLICATIONS

This application is a continuation-in-part of Ser. No. 770,544, filed Aug. 29, 1985, and now abandoned.

This invention is directed to an improved Fischer-Tropsch process for hydrocarbon synthesis operated in the fluid mode of the Sasol Synthol process to provide increased diesel and heavy hydrocarbon yield. In another aspect, it is directed to the utilization of Fischer-Tropsch synthesis catalysts modified by the presence of a minor amount of a zeolite catalyst.

In the Synthol version of the Fischer-Tropsch process, the catalyst particles are moving in a fluidized or entrained bed. This has many engineering and operating advantages over the use of a fixed bed, in particular with respect to temperature control, good mixing, heat removal, prevention of large temperature gradients, ease in changing or maintaining the desired catalyst, etc.

U.S. Pat. No. 4,046,829 is directed to a Fischer-Tropsch synthesis comprising separating the product into a fraction boiling above and below 400° F. and separately processing each over crystalline aluminosilicate zeolite. U.S. Pat. No. 4,052,477 is directed to a Fischer-Tropsch synthesis wherein a $C_{5+}$ fraction is separated, hydrogenated and contacted with a zeolite to obtain higher octane gasoline. U.S. Pat. No. 4,207,208 discloses single particle iron-containing syngas conversion catalysts comprising iron and a crystalline acidic aluminosilicate zeolite.

The patent and technical literature relating to the Fischer-Tropsch process is extensive and the various catalysts reported in the prior art have been used by themselves as well as in admixture with catalytically inactive supports such as kieselguhr. U.S. Pat. No. 4,086,262 is primarily directed to a multi-particle composite catalyst wherein the crystalline aluminosilicate component is physically admixed with a particulate Fischer-Tropsch catalytic component and to a process of converting synthesis gas to aromatics rich hydrocarbon mixtures or to hydrocarbon mixtures rich in liquifiable petroleum gases. In spite of the flexibility of these prior art processes, it has not been possible to efficiently and at relatively low cost to provide as great a quantity of high quality diesel fuels as is desired.

The present invention, therefore, is concerned with a Fischer-Tropsch process wherein diesel range hydrocarbon product yield is maximized comprising in a fluidized bed the simultaneous use of a Fischer-Tropsch synthesis catalyst and a zeolite catalyst of critical type, amount and activity such that the synthesis reactor operates at below the temperature minimum required in the prior art fluidized bed (Synthol) Fischer-Tropsch process, without loss of particle fluidization and flow characteristics. The zeolite catalyst must be of just sufficient activity and in just that relative amount to selectively convert enough waxy product to prevent adhesion between catalyst particles which otherwise might impede catalyst flow, and without causing extensive dewaxing conversion across the major portion of the boiling range of products.

More particularly, the process of the present invention is directed towards improving product yield, obtaining a larger yield of diesel fuel range materials, and improving operating economics of a synthesis gas conversion operation known in the industry as the Sasol process.

The Sasol process converts coal to hydrocarbons, oxygenates and chemical forming components. It is conveniently separated into (1) a synthesis gas preparation from coal, (2) a Fischer-Tropsch (F-T) type of synthesis gas conversion in both a fixed catalyst bed operation (ARGE Process) and a fluid catalyst bed operation (Synthol Process), (3) a product recovery operation and (4) product upgrading, refining and separation. The fixed bed process uses an expensive tube and shell heat exchange reactor and operates at temperatures between about 210°–230° C. It provides undesirably high amounts of paraffin waxes. The moving bed Synthol process is more economical but is limited to operating at temperatures of about 310°–330° C. and essentially all the product is in the gaseous state. Consequently light gases and gasoline are the major products. However, less than 10% diesel is typically contained in its products. The instant process is an improvement thereof producing up to 45% or more diesel.

The Sasol synthesis operation is known to produce a wide spectrum of products which amplify the complexity of the overall process arrangement and its operating economics. Aside from the hydrocarbon liquids which include gasoline, light and heavy fuels, fuel gas, light olefins, LPG and waxy oils, these are produced and identified as alcohols, aldehydes, ketones and acids (particularly acetic and proprionic acid). The $C_2$ and lower boiling components may be reformed to synthesis gas or they may be blended into a fuel gas pipeline system.

Propylene and butylene formed in the process can be further converted to fuel liquids as by polymerization in the presence of a solid phosphoric acid catalyst, which process produces primarily more gasoline. Higher amounts of gasoline can be made of involving zeolite catalysts either in combination with the Fischer-Tropsch synthesis operation, or in a subsequent conversion process involving certain parts or all of the synthesis product. Many such methods have been described. Current Fischer-Tropsch technology accordingly suffers from severe constraint on the relative amount of diesel fuel product compared to the volume of gasoline that can be produced.

In no case known to applicants has the use of zeolite in a Fischer Tropsch synthesis operation been suggested or utilized to increase the amount of diesel fuel relative to gasoline.

SUMMARY OF THE INVENTION

The present invention is concerned with improving a moving bed Fischer-Tropsch synthesis gas conversion operation such as the Synthol process wherein the product distribution is changed in favor of the diesel distillate range of utilizing the herein described modified Fischer-Tropsch catalyst. The improved process in accordance with this invention utilizes a specific range of conversion conditions, specific zeolite particle and granule sizes, and wherein Fischer-Tropsch catalysts are modified with specific zeolite percentages and alpha values. More particularly the present invention is concerned with improving the diesel and heavier distillate fuel yield of a Fischer-Tropsch type conversion operation.

Proper operation of the charge of moving catalyst particles places a restriction on the lowest temperature at which the Fischer-Tropsch synthesis can be operated. The synthesis process produces a wide range of hydrocarbons, ranging in molecular size from gases to waxy molecules. As the temperature is lowered there is an inherent tendency in the Fischer-Tropsch process to shift the distribution of products towards higher boiling materials. This would, in principle, result in a relatively larger diesel fuel fraction, except for the fact that more waxes are also made; and the highest molecular weight wax molecules are liquid under the operating conditions and tend to condense on the surface of catalyst particles. The coating of catalyst particles with wax leads to sticking and adhesion among particles which interferes with the free flow of the catalyst particles and leads to inoperability.

This represents a serious limitation to attempts to increase the fraction of heavier than gasoline type fuels such as diesel oils, by an economically advantageous fluidized bed process. Current trends toward more diesel production in view of this is actually forcing abandonment of the otherwise desirable fluid bed principle, and partial return to consideration of the fixed bed technology.

Accordingly, the present invention is particularly directed to a method for maximizing the production of diesel oil and heavier hydrocarbon oils from a suitable synthesis gas feed comprising operating a fluid mode Fischer-Tropsch synthesis process in the presence of a catalyst system comprising a major proportion of a Fischer-Tropsch synthesis catalyst modified with a minor proportion of a zeolite catalyst wherein the fraction of zeolite catalyst used, zeolite activity and the amount of liquid product produced are controlled so as to selectively convert or crack sufficient waxy product to prevent adhesion between catalyst particles, whereby catalyst fluidity is maintained and diesel oil and heavier hydrocarbon yield are maximized.

DESCRIPTION OF SPECIFIC EMBODIMENTS

A shape-selective zeolite catalyst component is added to a F-T synthesis catalyst charge such that just sufficient amounts of heavy wax molecules are selectively cracked to prevent laydown of wax on catalyst which would interfere with fluidization whereby the system is operated at lower than usual temperature conditions, obtaining a higher diesel distillate-to-gasoline ratio. Accordingly, the method in accordance with the invention maximizes the production of diesel oil and heavier hydrocarbons comprising operating a fluid mode Fischer-Tropsch synthesis process in the presence of a catalyst system comprising a major proportion of a Fischer-Tropsch synthesis catalyst and a minor proportion of an aluminosilicate zeolite catalyst having a silica to alumina ratio of at least 12, a constraint index of from about 1 to about 12 wherein the fraction of zeolite catalyst used, zeolite activity and the amount of liquid product produced under specified operating conditions of time, temperature and pressure are controlled in accordance with the following equation:

$$f.a.W = A.n$$

which is more fully described herein below, thereby selectively converting sufficient waxy product to prevent adhesion between catalyst particles, whereby catalyst fluidity is maintained.

It is to be understood that any suitable conventional Fischer-Tropsch catalyst may be used in this invention. Types of catalysts found useful in Fischer-Tropsch syntheses include but are not limited to, the following metals: iron, cobalt, ruthenium, thorium, osmium or rhodium, mixtures or suitable compounds thereof. Compounds especially preferred are iron oxides and iron carbides. The F-T catalysts may also comprise particles of any of the recited metals only or particles with minor amounts of K, Cu, Sn, P, W, rare earth, V, Mn, Mo, etc.

The zeolitic catalysts referred to herein are members of a special class of zeolites exhibiting some unusual properties. They are very active even with silica-to-alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g., of the X and A type. Furthermore, carbonaceous deposits, when formed, may be removed by burning at higher than usual temperatures to restore activity. In many environments the zeolites of this class exhibit very low coke forming capability, conducive of very long times on stream between burning regenerations.

An important characteristic of the crystal structure of this novel class of zeolites is that it provides a selective constrained access to and egress from the intracrystalline free space by virtue of having an effective pore size intermediate between the small pore Linde A and the large pore Linde X zeolites, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having higher ratios of at least 30. Such zeolites, after activation, acquire an intracrystalline sorption capacity for normal hexane which is greater than for water, i.e., they exhibit "hydrophobic" properties. It is believed that this hydrophobic characteristic is advantageous in the present invention.

The zeolites useful as catalysts in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Zeolites with windows of 10-membered rings are preferred, although in some instances excessive puckering of the rings or pore blockage may render these zeolites ineffective. Zeolites with windows of 12-membered rings do not offer sufficient constraint to produce advantageous conversions desired in the instant invention, although structures can be conceived due to pore blockage or other causes, that may be operative.

Rather than attempt to judge from crystal structure whether or not a zeolite possesses the necessary constrained access to molecules of larger cross-section than normal paraffins, a simple determination of the "Constraint Index" as herein defined may be made by continuously passing a mixture of an equal weight of normal hexane and 3-methylpentane over a smaller sample, approximately 1 gram or less, of zeolite at atmospheric pressure according to the following procedure. A sample of the zeolite catalyst of a particle size equal or less than that of coarse sand is mounted in a glass tube, pelleted or extruded catalyst is crushed to the desired small size. Prior to testing, the zeolite is treated with a stream of air at 1000° F. for at least 15 minutes. The zeolite is then flushed with helium and the reactor temperature is then adjusted to 600° F. The mixture of hydrocarbons is then passed at an hourly space velocity (i.e., volume of liquid hydrocarbon per volume of zeolite per hour) which will be sufficient to result in a conversion level of hydrocarbon of between 10% and 60%, over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| Zeolite | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of about 1 to 12.

Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials or hydrogen forms thereof.

ZSM-5 is described in greater detail in U.S. Patents No. 3,702,886 and Re 29,948. The entire descriptions contained within those patents, particularly the X-ray diffraction pattern of ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern, is incorporated herein by reference.

ZSM-23 is described in U.S. Pat. No. 4,076,842. The entire content thereof, particularly the specification and the X-ray diffraction pattern of the disclosed zeolite, is incorporated herein by reference.

ZSM-35 is described in U.S. Patent NOo 4,016,245 and ZSM-38 as described in U.S. Pat. No. 4,046,859, both of which are incorporated herein in their entirety by this reference.

ZSM-38 is described in U.S. Pat. No. 4,046,859 and is incorporated herein by reference.

ZSM-48 is described in U.S. Pat. No. 4,375,573 and Zeolite Beta in U.S. Patent Nos. 3,308,069 and RE 28,341. The entire contents of these three patents are incorporated herein by this reference.

Although the zeolites may contain silica and alumina, it is recognized that the silica and alumina portions may be replaced in whole or in part with other oxides. For example, $GeO_2$ is one of the art recognized substitutes for $SiO_2$, and $B_2O_3$, $Cr_2O_3$, $Fe_2O_3$ and $Ga_2O_3$ are art recognized replacements for $Al_2O_3$. Accordingly the term zeolite as used herein shall connote not only materials containing silicon and, optionally, aluminum atoms in the crystalline lattice structure thereof, but also materials which contain suitable replacement atoms for silicon and/or aluminum. U.S. Patent Nos. 4,269,813;

4,327,236; 4,285,919 and 4,331,641 describe the preparation of boron-containing ZSM-5 zeolite in which boron is introduced in the crystalline lattice structure. Great Britain Patent Application No. BG 2,024,790 describes modification of ZSM-5 type crystalline materials by which boron, chromium, beryllium, titanium, vanadium, manganese, iron, cobalt, zinc, zirconium, rhodium, silver, tin and antimony have entered the crystalline lattice of the silica in place of silicon. Introduction of boron and various other metals into the lattice structure of ZSM-5 is also discussed in Great Britain Patent Application No. GB 2,033,358. In addition, the described alumina-silica or metallo-silica or alumina-metallo zeolites may also contain such metals as phosphorus.

The conversion of synthesis gas in greater yield to the more desired valuable products of diesel fuel and heavier hydrocarbons is greatly enhanced by simultaneously employing the above-referred to crystalline aluminosilicate zeolites exemplified by ZSM-5 judiciously in a minor effective quantity, with a conventional Fischer-Tropsch catalyst. To achieve the proper conditions contemplated by the invention, it is necessary to have a limited amount of zeolite activity associated with the disclosed catalyst system. Typically the operation is carried out with solid catalyst particles comprising Fischer-Tropsch synthesis catalyst and a fraction (f) of zeolite catalyst, with the zeolite activity being $\alpha$ (alpha), and operating under conditions which produce (W), weights of liquid product per weight of total solid catalyst charge per hour, whereby these parameters are related by the condition that:

$$f \cdot \alpha \cdot W = A \cdot n$$

A is a characteristic number (see Table below), which depends on the temperature of operation, and n is a number from about 1 to about 10. The zeolite activity alpha ($\alpha$) is defined by its activity to crack n-hexane. Alpha is the value of the first order cracking rate constant for the particular sample relative to that of an equal volume of a standard amorphous silica-alumina catalyst, and measured at 538° C. The test has been described more fully in a paper by D. H. Olson, W. O. Haag, R. M. Lago, published in the Journal of Catalysis, Vol. 61, pp. 319-336, 1980 and in previous publications cited therein the comments of which are incorporated in their entirety by reference. The desired alpha activity of the zeolite can be varied by synthesizing it with a required or specific silica to alumina ratio as shown in the above referenced publication. Lower alpha value zeolites can be obtained by steaming or by deactivation with partial cation exchange, e.g., potassium or sodium ions. Alpha values (activity) from about 1 to about 200 may be used. Preferred are values from about 20 to about 150.

In the relationship outlined above, which characterizes the range of catalyst properties and operating conditions of this invention, the value of A will change or vary inversely with the average operating temperature approximately as follows:

TABLE

| Temperature, °C. | A |
|---|---|
| 190 to less than about 225 | 150 |
| 225 to less than about 250 | 18 |
| 250 to 300 | 2 to 3 |

It is an object of this invention to operate a modified Fischer-Tropsch process at lower temperatures than the prior art. For example, Sasol operates at temperatures of from about 310° C.+. The instant process is designed to operate at temperatures of 280° C. or less.

If W is 1 gram of liquid product per gram catalyst hour and the operating temperature is 250°-300° C., then A is 2-3 and since n is 1 to 10 A.n can be 2 to 30. Alpha is a given value for the particular zeolite if $\alpha$ is 60, then the fraction of zeolite to use is determined as follows:

$$f = \frac{A \cdot n}{\alpha \cdot W}$$

$$f = \frac{2}{60} \text{ to } \frac{30}{60} = 0.03 \text{ to } 0.5$$

Therefore, 3 to 50% of the total catalyst can be zeolite.

The novel conversion of syngas, or synthesis gas, i.e., mixtures of gaseous carbon oxides with hydrogen or hydrogen donors to hydrocarbon mixtures and oxygenates, in accordance with the disclosed process is carried out at temperatures ranging from about 190°–300° C. and more particularly from 200° C. to about 280° C. at gas hourly space velocities (GHSV), ranging from about 250 to 20,000 and more desirably from about 350 to about 6,000, based on fresh feed and total catalyst volume. The rate of liquid product generation is typically between 0.5 and 5 weight/weight of catalyst charge/hr. Hydrogen to carbon oxides ratios can vary from 0.5:1 to 2:1 and more preferably are about 1:1, pressures ranging from about 3 to about 70 atmospheres and more preferably from about 10 to about 35 atmospheres are employed. Any suitable Fischer-Tropsch feed (stream) may be used as long as it contains substantial amounts of syngas, i.e., hydrogen and carbon oxygenates such as CO and $CO_2$.

Since it is important to effect conversion of the heaviest fraction of wax, the catalyst particle size, zeolite crystal size will preferably be as small as possible. Suitable zeolite crystalline size can vary from about 0.01 to about 1 $\mu$m (micrometer) and preferably from about 0.2 to about 0.1 $\mu$m. Fluidized granule sizes thereof can vary from less than about 0.1 $\mu$m to about 1.0 mm. Preferred are sizes from about 10 to about 150 $\mu$m. This is particularly true for mechanical mixtures of the catalyst charge.

It is possible under proper circumstances and desirable to make a composite catalyst particle of both zeolite and metal-synthesis composition, with activities and relative amounts otherwise similar to the above descriptions.

Care must be taken that the process conditions are strictly adhered to or the resulting product will not be the desired predominantly heavier liquids. The use of the zeolite allows the synthesis to be carried out at lower temperatures than otherwise possible. The selection of certain level of zeolite activity (alpha) is necessary to insure only a limited amount of activity, that is, just enough activity to prevent wax coating of the catalyst particles. The action of the catalyst materials assures operability at the lower temperature, while such lower temperature condition promotes a product distribution with significantly higher proportions of heavier liquids, such as diesel oil, than would be obtained at the temperature of the conventional synthesis in absence of zeolite catalyst.

Generally speaking, the modified catalyst system will contain up to about 96 wt. % or preferably from about 60 to about 90% or more of the F-T catalyst and from about 2 to about 20% of the zeolite catalyst depending, inter alia, upon operating parameters. However, the weight or volume ratio of F-T catalyst to zeolite can vary from 100 to 1 and preferably about 30 to 1 to about 5 to 1. Resultant yields of diesel oil will comprise at least 15–20 wt. % diesel oil based on the total liquid product produced. However, higher yields of 30% and up to 45% or more of diesel oil are possible if all factors are indeed maximized. The diesel oil produced will normally have an initial boiling point of about 165° C. and an end point of about 400° C. and preferably boiling between about 210 and about 350° C. Prior art methods generally produce 10%–12% or less of diesel oil, as disclosed in an article by M. E. Dry, Research Department SASOL. Sasolburg, South Africa in Catalysis: Science and Technology, 1981, 1, 159–255, Anderson and Boudart, Eds.

It will be useful to use zeolite components which have been exposed to ion exchange with monovalent metals or alkali metals such as K, Na, Ce and Ru, in order to prevent further loss and migration of such metallic ions from, for example, iron-containing Fischer-Tropsch catalyst having minor amounts thereof. Potassium ion-exchange is preferred. The migration of potassium and other such metals away from the Fischer-Tropsch catalyst component to the zeolite can also be inhibited by providing the zeolite with cations with possess much higher affinities to, e.g., aluminum sites than does the potassium ion. This is accomplished by providing the zeolite component with multivalent ions that occupy most of the cationic exchange sites of aluminum. Thus the calcium form, or other alkaline earth metal ions are attractive examples. Exchange with rare earth metals such as lanthanum or cerium is also attractive.

The particle size and density differences between the particles of F-T synthesis catalyst and those of the zeolite containing component can be favorably utilized in the fluid bed or entrained bed reaction system, to separate the two components to such an extent as to enable control of make-up rates individually.

The following examples illustrate without limiting the novel process of this invention.

EXAMPLE 1

An iron-containing, i.e., fused magnetite $Fe_3O_4$, Fischer-Tropsch catalyst composition is operated in the Fischer-Tropsch synthesis mode at 230° C., using a CO/hydrogen ratio of 1:2, and a sufficient gas flow rate to generate 2 weights of liquid product per weight of catalyst per hour. The molecular weight distribution of the liquid product is determined by conventional liquid/vapor chromatography. The ratio of products above that corresponding to $C_{16+}$ hydrocarbon waxes, and the amount of liquid below that molecular weight are determined by any convenient means. This ratio was so high that catalyst particles agglomerated or struck together, causing low conversion rates and loss of fluidity of catalyst system.

EXAMPLE 2

An iron-containing Fischer-Tropsch catalyst composition as described in Example 1 is mechanically mingled with ZSM-5 catalyst particles in proportion comprising 70% of the former and 15% of ZSM-5 zeolite of an alpha activity of 140. The combined material is charged to a reactor and operated in the Fischer-Tropsch synthesis mode at 230° C., using a hydrogen/CO ratio of 2:1, and a sufficient gas flow rate to generate 2 weights of liquid product per weight of catalyst per hour. The molecular weight distribution of the liquid product is determined by conventional liquid/vapor chromatography. The ratio of products above that corresponding to $C_{16+}$ hydrocarbons to the amount of liquid below that molecular weight is also determined. It was found to be appreciably lower than in the case of Example 1, and sufficiently low enough to avoid the sticking together of catalyst particles by $C_{16+}$ hydrocarbon waxes. The value of $f\alpha W$ calculates to be 42.

EXAMPLE 3

A similar (Example 1) iron-containing Fischer-Tropsch catalyst composition is mechanically mingled with ZSM-5 catalyst particles in proportion comprising 96% of the former and 2% of ZSM-5 zeolite of an alpha activity of 60. The combined material is charged to a reactor and operated in the Fischer-Tropsch synthesis mode at 270° C., using a hydrogen/CO ratio of 2:1, and a sufficient gas flow rate to generate 2 weights of liquid product per weight of catalyst per hour. The molecular weight distribution of the liquid product is determined by conventional liquid/vapor chromatography. The ratio of products above that corresponding to $C_{16+}$ hydrocarbons, to the amount of liquid below that molecular weight is determined. This ratio was found to be significantly lower than in Example 1, and low enough to prevent the sticking of catalyst particles. The value of $f\alpha W$ calculates to be 2.4.

EXAMPLE 4

A similar (Example 1) iron-containing Fischer-Tropsch catalyst composition is mechanically mingled with ZSM-5 catalyst particles in proportion comprising 50% of the former and 35% of ZSM-5 zeolite of an alpha activity of 140. The combined material is charged to a reactor and operated in the Fischer-Tropsch synthesis mode at 260° C., using a hydrogen/CO ratio of 2:1, and a sufficient gas flow rate to generate 2 weights of liquid product per weight of catalyst per hour. The molecular weight distribution of the liquid product is determined by conventional liquid/vapor chromatography. The ratio of products above that corresponding to $C_{16+}$ hydrocarbons, to the amount of liquid below that molecular weight is determined. It was found to be significantly lower than in Example 1; but also, the amount of diesel boiling range product is significantly decreased at the expense of greater production of gasoline and gases. The calculated value of $f\alpha W$ in this case is about 100, and is greater than desired to maximize heavier hydrocarbon and diesel fuel production at this operating temperature.

EXAMPLE 5

A cobalt-containing Fischer Tropsch catalyst composition containing 100 parts by weight of cobalt, 8 parts by weight of MgO, 5 parts by weight of $ThO_2$ and 200 parts by weight of Kieselguhr prepared from a solution of corresponding metal nitrates. 40 grams of cobalt per liter of solution are added at 100° C. to a solution of 100 grams of Na₂CO'hd 3 per liter with vigorous stirring. The required amount of Kieselguhr is then added to the mixture which is filtered and washed with hot water and extruded after crushing to desired mesh size of about 100 microns. It is then reduced at a temperature of about 400° C. for two hours. The thusly prepared cobalt containing catalyst is then mechanically mingled with ZSM-5 catalyst particles in proportion comprising about 60 percent cobalt and 20 percent XSM-5 with an alpha activity of 100. The combined material is charged to a reactor and operated in the Fischer Tropsch synthesis mode at about 240° C., using a hydrogen/CO ratio of 2:1, and a sufficient gas flow rate to generate 2 weights of liquid product per weight of catalyst per hour. The molecular weight distribution of the liquid product is determined by conventional liquid/vapor chromatography. The ratio of products above that corresponding to $C_{16+}$ hydrocarbons to the amount of liquid below that molecular weight is also determined. It was found to be appreciably lower than in the case of Example 1, and sufficiently low enough to avoid the sticking together of catalyst particles by $C_{16+}$ hydrocarbon waxes. The value of F $\alpha$w calculates to be 20.

The above-described exemplary material clearly illustrates that the novel Fischer-Tropsch process in accordance with the invention provides increased yields of diesel oil and heavier hydrocarbons. However, it is to be understood that the catalysts may not only be mixed so as to allow simultaneous contact with the feedstream but may also be arranged in any manner known to the art which will allow the zeolite catalyst to be downstream of the F-T catalyst in the fluidized catalyst bed.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for maximizing the production of diesel oil and heavier hydrocarbon oils comprising contacting a suitable synthesis gas feed comprising hydrogen and carbon oxides with a fluidized or moving bed catalyst system comprising a major proportion of a Fischer-Tropsch synthesis catalyst containing a minor proportion of a zeolite catalyst having an alpha value of from 1 to about 200 and wherein the fraction of zeolite catalyst used, zeolite activity and the amount of liquid product produced are controlled in accordance with the following equation:

$$f.alpha.W + A.n$$

where f is the fraction of zeolite catalyst used, alpha is zeolite activity, W is the weigh of liquid product per weight of total solid catalyst charge per hour, A is an average number which varies inversely with the operating temperature and n is from about 1 to 10, thereby selectively converting or cracking sufficient waxy product also produced to prevent adhesion between catalyst particles, maintaining catalyst fluidity and maximizing diesel oil and heavier hydrocarbon yield.

2. The process of claim 1 wherein said liquid product contains at least about 15 wt. % diesel oil based on the total weigh of said product.

3. The process of claim 1 wherein said liquid product contains at least about 20 wt. % diesel oil.

4. The process of claim 1 wherein said liquid product contains 45 wt. % or more of diesel oil.

5. The process of claim 1 wherein the temperature varies from about 190 to about 300° C. at a GHSV ranging from about 250 to 20,000, W is between about 0.5 and 5 weights/weight of catalyst charge/hour at pressures ranging from about 3 to about 70 atmospheres.

6. The process of claim 5 wherein the temperature varies from about 220° to about 280° C.

7. The process of claim 1 wherein the diesel oil produced boils between about 165°–400° C.

8. The process of claim 6 wherein the diesel oil produced boils between about 210°–350° C.

9. The process of claim 1 wherein the alpha value varies from about 1 to about 200.

10. The process of claim 9 wherein the alpha value varies from about 20 to about 150.

11. The process of claim 1 wherein the major proportion varies from about 60 to about 96% and said minor proportion varies from about 2 to about 20%.

12. The process of claim 1 wherein the Fischer Tropsch synthesis catalyst is selected from the group consisting essentially of the following metals: iron, cobalt, ruthenium, thorium, rhodium, osmium, mixtures thereof, and suitable compounds thereof, wherein said metals or compounds thereof also contain minor amounts of K, Sn, P, W, rare earths, V, Mn or Mo.

13. The process of claim 12 wherein the ratio of Fischer-Tropsch catalyst to zeolite catalyst varies from about 30 to 1 to about 5 to 1.

14. The process of claim 13 wherein the F-T catalyst is selected from the group consisting of iron, iron oxide or iron carbide.

15. The process of claim 14 wherein said F-T catalyst contains minor amounts of K, Sn, P24., rare earths, V, Mn or Mo.

16. The process of claim 1 wherein the zeolite catalyst is selected from the group consisting essentially of ZSM-6, ZSM-11, ZSM-12, ZSM-22, ZSM-23, ZSM-35, ZSM-38, ZSM-48 or hydrogen forms thereof.

17. The process of claim 16 wherein the zeolite catalyst is ZSM-5.

18. The process of claim 1 wherein the zeolite catalyst has a silica to alumina ratio of at least 12 and a constraint index of from about 1 to about 12.

19. The process of claim 17 wherein the silica and/or alumina may be replaced in whole or in part by oxides from the group consisting essentially of boron, chromium, beryllium, titanium, vanadium, manganese, iron, cobalt, zinc, zirconium, rhodium, silver, tin, antimony, gallium and germanium and various mixtures thereof.

20. The process of claim 19 wherein the zeolite has been ion exchanged with multivalent ions selected from the group consisting of alkaline earth metal or rate earth metal ions.

21. The process of claim 19 wherein the zeolite has been ion exchanged with monovalent ions selected from the group consisting of alkali metal ions.

22. The process of claim 20 wherein the alkali metal is potassium.

23. The process of claim 1 wherein said synthesis gas feed contains said hydrogen and carbon oxide or oxides in a ratio of from about 0.5:1 to about 2:1.

24. The process of claim 23 wherein said feed ratio is about 1:1.

25. The process of claim 23 wherein said ratio is 2:1.

26. The process of claim 25 wherein the operating temperature is about 230° C. and the catalyst system comprises 70% F-T catalyst, and 15% zeolite catalyst with an alpha value of about 140.

27. The process of claim 25 wherein the temperature is 270° C. and the catalyst system comprises 96% Fischer-Tropsch catalyst and 2% zeolite catalyst with an alpha of 60.

28. The process of claim 26 wherein the value of f alpha W calculates to be about 42.

29. The process of claim 27 wherein the value of f alpha W calculates to be about 2.4.

30. The process of claim 26 wherein the zeolite catalyst is ZSM-5.

31. The process of claim 27 wherein the zeolite catalyst is ZSM-5.

32. The process of claim 26 wherein said catalysts are mechanically mingled.

33. The process of claim 27 wherein said catalysts are mechanically mingled.

34. In a Fischer-Tropsch process for maximizing the production of diesel oil and heavier hydrocarbon oil, the improvement comprising contacting a synthesis gas feed comprising hydrogen and carbon monoxide with a fluidized or moving bed catalyst system comprising a major amount of a Fischer-Tropsch synthesis catalyst and a minor amount of a zeolite catalyst having an alpha value of from about 1 to 200 wherein the fraction of zeolite catalyst used, zeolite activity and the amount of liquid product produced are controlled in accordance with the following equation:

$$f.alpha.W = A.n$$

where f is the fraction of zeolite catalyst used, alpha is zeolite activity, W is the weight of liquid product per weight of total solid catalyst charge per hour, A is an average number which varies inversely with the operating temperature and n is from about 1 to 10, thereby selectively converting or cracking sufficient waxy product also produced to prevent adhesion between catalyst particles, maintaining catalyst fluidity and maximizing diesel oil and heavier hydrocarbon yield.

* * * * *

UNITED STATES PATENT AND TRADEMARK OFFICE
CERTIFICATE OF CORRECTION

PATENT NO. : 4,906,671
DATED : March 6, 1990
INVENTOR(S) : Werner O. Haag et al

It is certified that error appears in the above-identified patent and that said Letters Patent is hereby corrected as shown below:

Col. 8, line 30      Delete [200°], insert --220°--

Col. 11, line 3      Delete [$Na_2CO'hd\ 3$], insert --$Na_2CO_3$--

Col. 12, line 42, claim 15 Delete [P24.,], insert --P, W,--

Col. 12, line 46, claim 16 Delete [ZSM-6], insert --ZSM-5--

Signed and Sealed this

Twenty-seventh Day of August, 1991

Attest:

HARRY F. MANBECK, JR.

Attesting Officer      Commissioner of Patents and Trademarks